US009926528B2

(12) United States Patent
Lee

(10) Patent No.: US 9,926,528 B2
(45) Date of Patent: Mar. 27, 2018

(54) GLUCOMANNAN SCAFFOLDING FOR THREE-DIMENSIONAL TISSUE CULTURE AND ENGINEERING

(71) Applicant: The Regents of the University of California, Oakland, CA (US)

(72) Inventor: C. Chang I Lee, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 84 days.

(21) Appl. No.: 15/169,521

(22) Filed: May 31, 2016

(65) Prior Publication Data

US 2017/0029764 A1 Feb. 2, 2017

Related U.S. Application Data

(63) Continuation of application No. 14/360,910, filed as application No. PCT/US2012/066982 on Nov. 29, 2012, now Pat. No. 9,359,591.

(60) Provisional application No. 61/564,553, filed on Nov. 29, 2011.

(51) Int. Cl.
| | |
|---|---|
| *C08B 37/00* | (2006.01) |
| *C12N 5/00* | (2006.01) |
| *C12N 5/0775* | (2010.01) |
| *C08L 5/00* | (2006.01) |
| *C08J 9/28* | (2006.01) |
| *C08J 9/36* | (2006.01) |
| *C12N 5/074* | (2010.01) |

(52) U.S. Cl.
CPC ........ *C12N 5/0068* (2013.01); *C08B 37/0087* (2013.01); *C08J 9/28* (2013.01); *C08J 9/36* (2013.01); *C08L 5/00* (2013.01); *C12N 5/0607* (2013.01); *C12N 5/0663* (2013.01); *C08J 2201/0484* (2013.01); *C08J 2207/10* (2013.01); *C08J 2305/00* (2013.01); *C12N 2513/00* (2013.01); *C12N 2533/70* (2013.01)

(58) Field of Classification Search
None
See application file for complete search history.

(56) References Cited

U.S. PATENT DOCUMENTS

| 6,379,962 B1 | 4/2002 | Holy et al. |
| 2004/0209359 A1 | 10/2004 | Yayon et al. |
| 2006/0233850 A1 | 10/2006 | Michal |
| 2010/0255076 A1 | 10/2010 | Heber et al. |

FOREIGN PATENT DOCUMENTS

| CN | 101322857 A | 12/2008 |
| CN | 101322858 A | 12/2008 |
| JP | S59-169462 A | 9/1984 |
| JP | 2005-290610 A | 10/2005 |
| WO | 2010/113516 A1 | 10/2010 |

OTHER PUBLICATIONS

Alonso-Sande, et al., "Glucomannan, a promising polysaccharide for biopharmaceutical purposes," *Eur J Pharm Biopharm.*, vol. 72, pp. 453-462 (2009).
Herranz, et al., "Effect of alkalis on konjac glucomannan gels for use as potential gelling agents in restructured seafood products," *Food Hydrocolloids*, vol. 27, No. 1, pp. 145-153 (2012).
Karageorgiou, et al., "Porosity of 3D biomaterial scaffolds and osteogenesis," *Biomaterials*, vol. 26, pp. 5474-5491 (2005).
Kondo, et al., "Konjac glucomannan-based hydrogel with hyaluronic acid as a candidate for a novel scaffold for chondrocyte culture," *J Tissue Eng Regen Med.*, vol. 3, pp. 361-367 (2009).
Konishi, et al., "Mode of Rat Cecal Enlargement Induced by a Short-term Feeding on Glucomannan," *Jpn J Exp Med.*, vol. 54, pp. 139-142 (1984).
Liu, et al. "Synthesis, Characterization, and Evaluation of Phosphated Cross-Linked Konjac Glucomannan Hydrogels for Colon-Targeted Drug Delivery," *Drug Deliv.*, vol. 14, pp. 397-402 (2007).
Nie, et al., "Electrospinning and characterization of konjac glucomannan/chitosan nanofibrous scaffolds favoring the growth of bone mesenchymal stem cells," *Carbohydrate Polymers*, vol. 85, No. 3, pp. 681-686 (2011).
Nishinari, et al., "Storage Plant Polysaccharides: Xyloglucans, Galactomannans, Glucomannans," *Comprehensive Glycoscience*, vol. 2, pp. 613-652 (2007).
Wang, et al. "Alginate-konjac glucomannan-chitosan beads as controlled release matrix," *Int J Pharm.*, vol. 24, pp. 117-126 (2002).
Wen, et al., Preparation of konjac glucomannan hydrogels as DNA-controlled release matrix, *Int J Biol Macromol.*, vol. 42, pp. 256-263 (2008).
Ye, et al., "Condensed state structure and biocompatibility of the konjac glucomannan/chitosan blend films," *Carbohydrate Polymers*, vol. 64, No. 4, pp. 532-538 (2006).
Yuan, et al., "A preliminary study on osteoinduction of two kinds of calcium phosphate ceramics." *Biomaterials*, vol. 20, pp. 1799-1806 (1999).
European Search Report from European Application No. 12853122.5. dated Aug. 5, 2015.
International Search Report and Written Opinion for PCT/IS2012/066982 dated Feb. 5, 2013.
Office Action from China Application No. 201280058878.X dated Apr. 30, 2015 with English translation.
Office Action from Japanese Application No. 2014-544866 dated Jul. 12, 2016 with English translation.
First Examination Report from European Application No. 12853122.5. dated May 2, 2016; 4 pages.
Badillo, G.M. et al.; "Theoretical and experimental aspects of vacuum impregnation of porous media using transparent etched networks"; International Journal of Multiphase Flow; Jun. 6, 2011; pp. 1219-1226; vol. 37, No. 9; Elsevier; Amsterdam, NL.

*Primary Examiner* — David W Berke-Schlessel
(74) *Attorney, Agent, or Firm* — Mintz, Levin, Cohn, Glovsky and Popeo, P.C.

(57) ABSTRACT

The present invention provides a neutralized glucomannan scaffold capable of promoting cell growth and suitable for three-dimensional tissue culture and engineering. The present invention also provides methods for making and degrading the neutralized glucomannan scaffold. The present invention further provides a method of growing cells on a neutralized glucomannan scaffold.

20 Claims, 12 Drawing Sheets

GLUCOMANNAN SCAFFOLDING FOR THREE-DIMENSIONAL TISSUE CULTURE AND ENGINEERING

CROSS-REFERENCE TO RELATED APPLICATIONS

This application is a continuation of U.S. application Ser. No. 14/360,910, filed May 27, 2014, which is the National Stage of International Application No. PCT/US2012/066982, which claims the benefit of U.S. Provisional Application No. 61/564,553, filed Nov. 29, 2011, which is incorporated in its entirety herein for all purposes.

BACKGROUND OF THE INVENTION

Engineering biomaterials to repair damaged or diseased tissues such as cardiac, bone, liver, corneal and skin is an active branch of research in regenerative medicine. One approach being investigated is using cells combined with biomaterial constructs, or scaffolds, that facilitate cell growth and differentiation to create functional tissues in vitro that can be implanted. Three-dimensional (3D) tissue culture systems, which emulate key physical and molecular features of the extracellular microenvironment, provide tremendous advantages to tissue engineering.

Biomaterials may be naturally-derived, such as protein- and polysaccharide-based biomaterials, or synthetic, for example, polymer-, peptide- and ceramic-based biomaterials. Rigorous exploration of properties such as immunogenicity, biodegradability, biocompatibility, ease of modification and permeability is required for the design and development of these biomaterials for clinical tissue engineering. High porosity and adequate pore size, in particular, are important for cell seeding and diffusion of cells and nutrients.

The ready availability and biocompatibility of natural biomaterials such has collagen, alginate and chitosan have made these natural biomaterials attractive substrates for 3D tissue culture. However, challenges with inconsistent mechanical properties and behavior of seeded cells limit their clinical application.

For bone engineering, porosity and pore size of scaffolds have been shown to be a critical factor. Prior studies have indicated that larger pores (~200-300 µm) result in larger surface area that may promote ion/gas exchange, protein adsorption, and bone apatite mineralization (Karageorgiou et al. *Biomaterials* 2005 26:5474-91; Yuan et al. *Biomaterials* 1999 20:1799-806). It is also thought that a larger pore size may be necessary to vascularize implants and mimic the cortical surface and cancellous interior of natural bone (Karageorgiou et al. *Biomaterials* 2005 26:5474-91). As such, there is a need for scaffolds with large pores that can be seeded with bone cells and used for bone regeneration.

Glucomannan is a naturally-derived polysaccharide composed of a 1:1.6 ratio of β-1,4 linked D-glucose to D-mannose with branches approximately every 11 residues (Alonso-Sande et al. *Eur J Pharm Biopharm*. 2009 72:453-62). Glucomannan has a backbone of approximately 5-10% substituted acetyl groups that participate in hydrogen bonding and hydrophobic interactions that confers solubility. Hydrolysis of the acetyl group in the presence of alkali decreases the solubility of glucomannan and results in aggregation followed by gel formation. Glucomannan is commonly used in foods as an emulsifier or thickener and is being investigated for biopharmaceutical applications due to its gelling and biodegradable properties as well as its malleability to be shaped into films, beads and hydrogels. Glucomannan-based beads, microparticles, and nanoparticles have been developed for DNA and drug delivery (Liu et al. *Drug Deliv.* 2007 14:397-402; Wang et al. *Int J Pharm.* 2002 244:117-26; Wen et al. *Int J Biol Macromol.* 2008 42:256-63) with no significant signs of oral toxicity, skin sensitization, intestinal toxicity, embryotoxicity, or cell-aging observed (Konishi et al. *Jpn J Exp Med.* 1984 54:139-42).

Glucomannan has recently been investigated as composite scaffolds for chondrocyte culture and injectable scaffolds for cartilage regeneration (Kondo et al. *J Tissue Eng Regen Med.* 2009 3:361-7). This investigation resulted in the production of a konjac glucomannan/hyaluronic acid hydrogel, wherein cells are cultured and allowed to clump as a suspension in the gel. However, an exploration of developing glucomannan as a porous scaffold for tissue engineering applications has yet to be conducted.

Surprisingly, the present invention provides a glucomannan microporous matrix capable of promoting cell growth and useful as a novel biomaterial scaffold for 3D cell culture and tissue engineering as well as in vivo tissue regeneration, for example, bone regeneration.

BRIEF SUMMARY OF THE INVENTION

It has been found that when a basic glucomannan scaffold is neutralized, the resulting neutralized glucomannan scaffold is useful as a matrix for three-dimensional (3D) cell culture and tissue engineering. The neutralized glucomannan scaffold has a pH that is suitable for efficient cell growth, and a porous structure that can permit diffusion of oxygen, nutrients, expressed products and cellular waste. Moreover, the neutralized glucomannan scaffold of the invention is amenable to surface modification to promote cell adhesion and proliferation. This naturally-derived biomaterial scaffold is thermally stable, non-toxic and biodegradable and may mimic the natural three-dimensional microenvironment of a wide range of cell types, such as osteoblasts, heptocytes, lymphocytes and stem cells.

In other embodiments, the present invention provides a method of preparing a neutralized glucomannan scaffold, including contacting a basic glucomannan scaffold having a pH of greater than about 8 with an aqueous solution at a pressure greater than or about atmospheric pressure, to form the neutralized glucomannan scaffold having a pH of about 7, thereby preparing the neutralized glucomannan scaffold.

In one embodiment, the present invention provides a method of preparing a neutralized glucomannan scaffold, including contacting a basic glucomannan scaffold having a pH of greater than about 8 with an aqueous solution under vacuum pressure, to form the neutralized glucomannan scaffold having a pH of about 7, thereby preparing the neutralized glucomannan scaffold.

In another embodiment, the present invention provides a method of growing cells on a neutralized glucomannan scaffold, including heating a reaction mixture of the neutralized glucomannan scaffold of the present invention and a cell, such that the cell multiplies, thereby growing cells on the neutralized glucomannan scaffold.

In another embodiment, the present invention provides a neutralized glucomannan scaffold, prepared by contacting a basic glucomannan scaffold having a pH of greater than about 8, with an aqueous solution to form the neutralized glucomannan scaffold having a pH of about 7.

In another embodiment, the present invention provides a neutralized glucomannan scaffold, prepared by contacting a basic glucomannan scaffold having a pH of greater than about 8, with an aqueous solution at a pressure greater than or about atmospheric pressure, to form the neutralized glucomannan scaffold having a pH of about 7, wherein the basic glucomannan scaffold comprises a cell adhesion promoter.

In a further embodiment, the present invention provides a method of degrading the neutralized glucomannan scaffold of the present invention by contacting the neutralized glucomannan scaffold with a degrading agent.

DETAILED DESCRIPTION OF THE INVENTION

I. Definitions

Figure 1A:
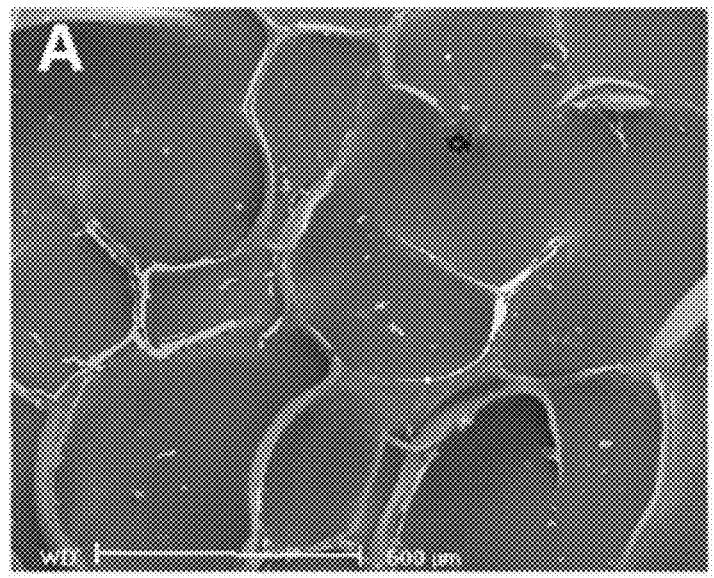
FIG. 1A shows a scanning electron micrograph (surface topology) of the surface of a glucomannan gel after sublimation of water.
Figure 1B:
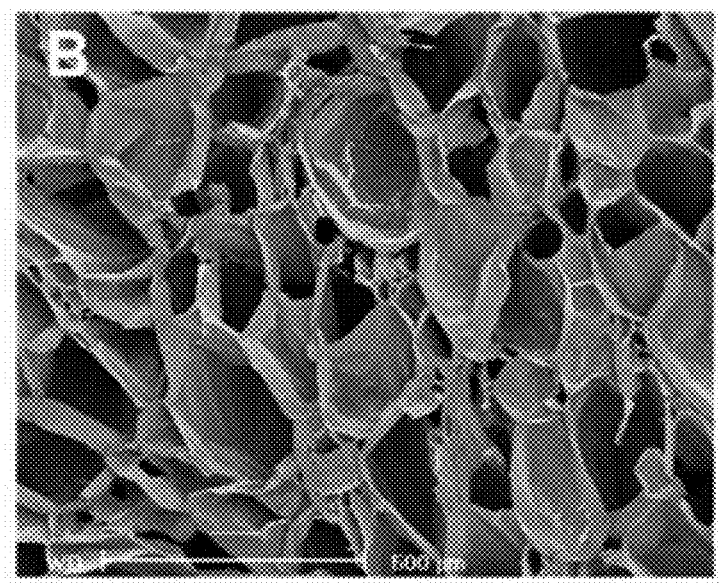
FIG. 1B shows a scanning electron micrograph (surface topology) of the surface of the inner structure of a glucomannan gel after sublimation of water.
Figure 1C:
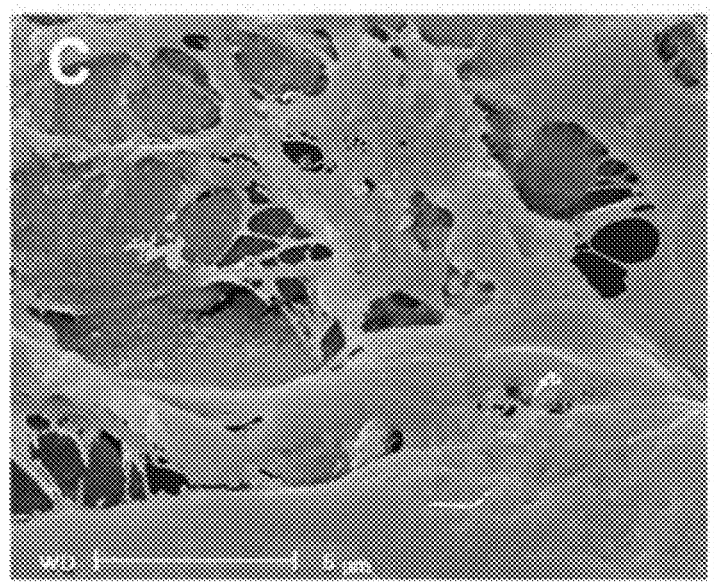
FIG. 1C shows a scanning electron micrograph (surface topology) of human mesenchymal stem cells (hMSC) seeded onto a glucomannan scaffold.
Figure 1D:
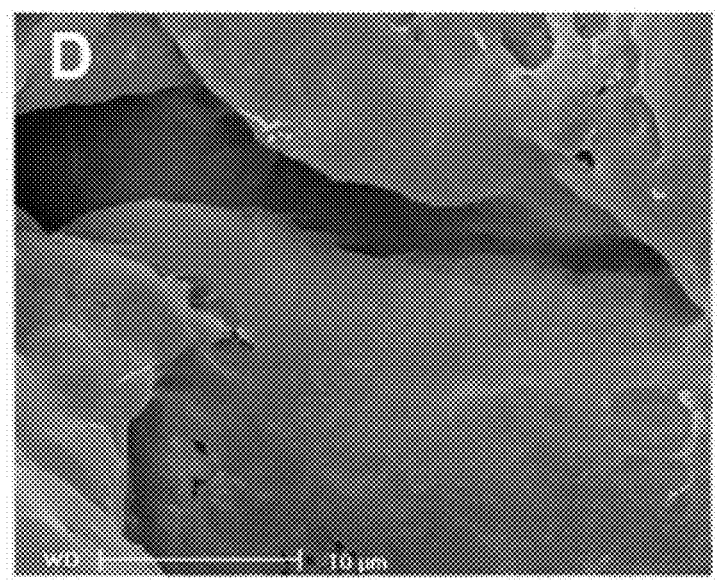
FIG. 1D shows a scanning electron micrograph (surface topology) of human mesenchymal stem cells (hMSC) seeded onto a glucomannan scaffold.
Figure 2:
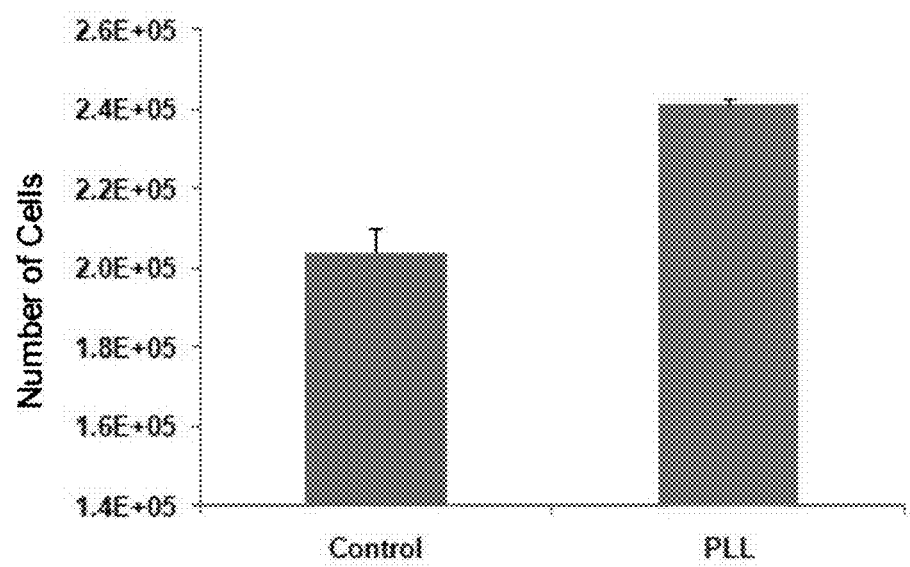
FIG. 2 shows the effects of poly-L-lysine (PLL) on the adherence of hMSC. PLL was added to the glucomannan mixture prior to gelling. hMSC showed a significantly greater attachment to the resulting scaffold compared to control ($p<0.05$).
Figure 3A:
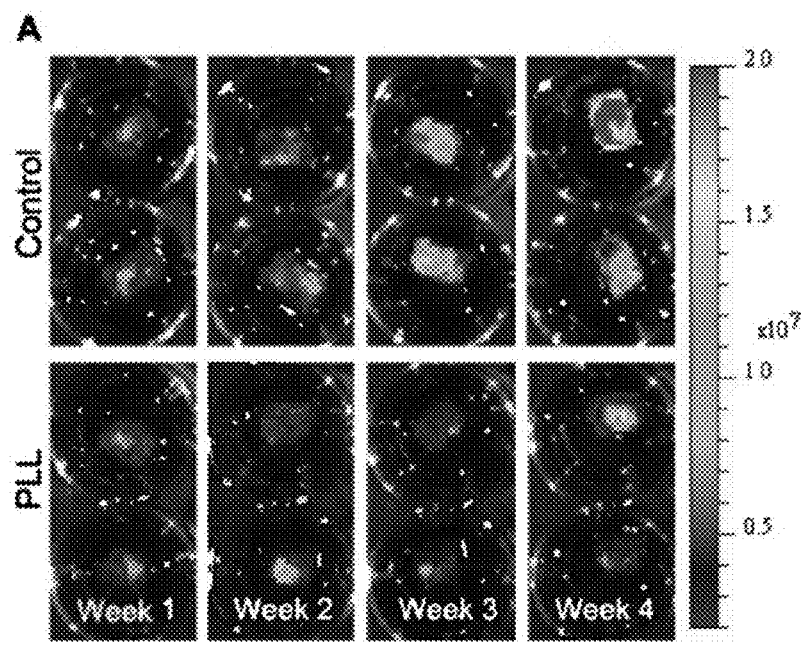
FIG. 3A shows bioluminescence images of hMSC cultured in the glucomannan scaffold. hMSC expressing firefly luciferase were seeded onto control or PLL-treated glucomannan scaffolds and imaged weekly. Cells cultured in control scaffolds showed an increase in the level of bioluminescence over time. However, hMSC cultured in glucomannan scaffolds were restricted to the site of seeding and showed no increase in bioluminescence.
Figure 3B:
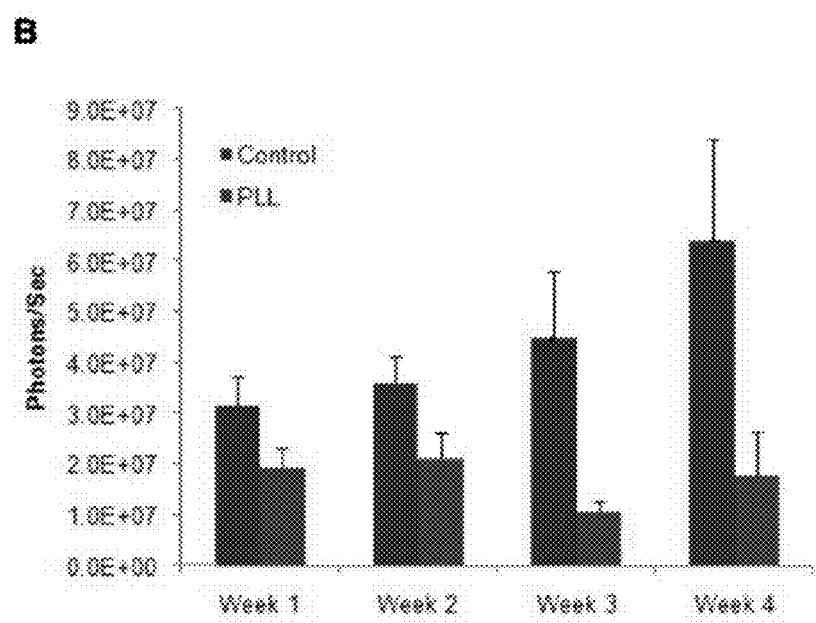
FIG. 3B shows bioluminescence photons per second data of hMSC cultured in the glucomannan scaffold. hMSC expressing firefly luciferase were seeded onto control or PLL-treated glucomannan scaffolds and imaged weekly. Cells cultured in control scaffolds showed an increase in the level of bioluminescence over time. However, hMSC cultured in glucomannan scaffolds were restricted to the site of seeding and showed no increase in bioluminescence.
Figure 4A:
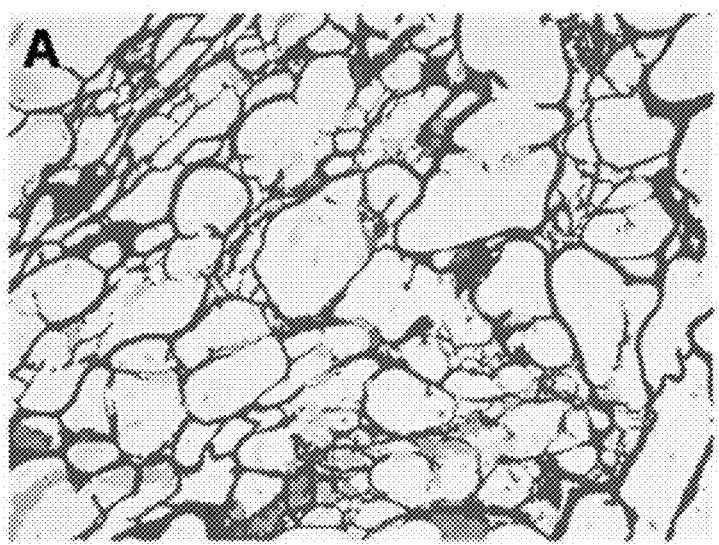
FIG. 4A shows porous structures [200-300 µm] throughout a glucomannan scaffold prior to seeding (10× magnification).
Figure 4B:
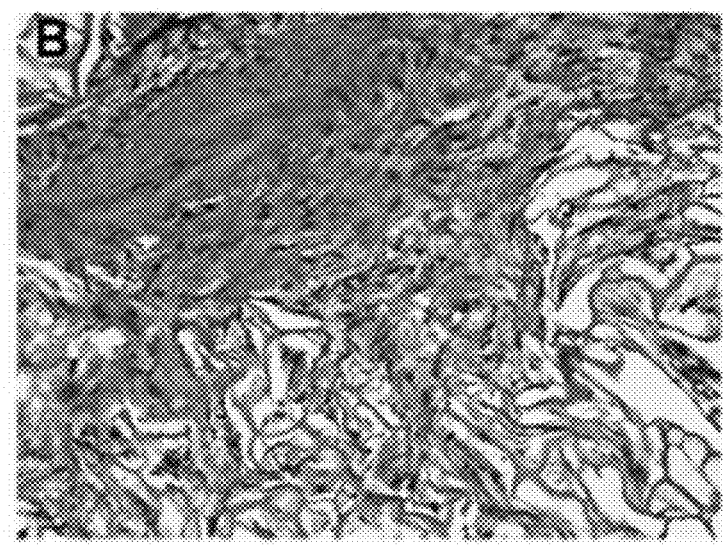
FIG. 4B shows an example structural morphology of hMSC seeded in the glucomannan scaffold (10× magnification). hMSC cultured in glucomannan scaffolds were stained with hematoxylin and eosin.
Figure 4C:
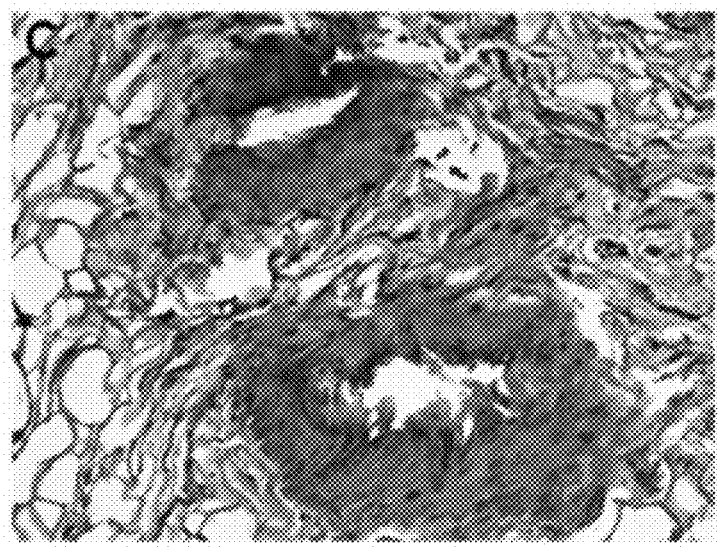
FIG. 4C shows an example structural morphology of hMSC seeded in the glucomannan scaffold (10× magnification). hMSC cultured in glucomannan scaffolds were stained with hematoxylin and eosin.
Figure 4D:
FIG. 4D shows an example structural morphology of hMSC seeded in the glucomannan scaffold (10× magnification). hMSC cultured in glucomannan scaffolds were stained with hematoxylin and eosin.
Figure 5:
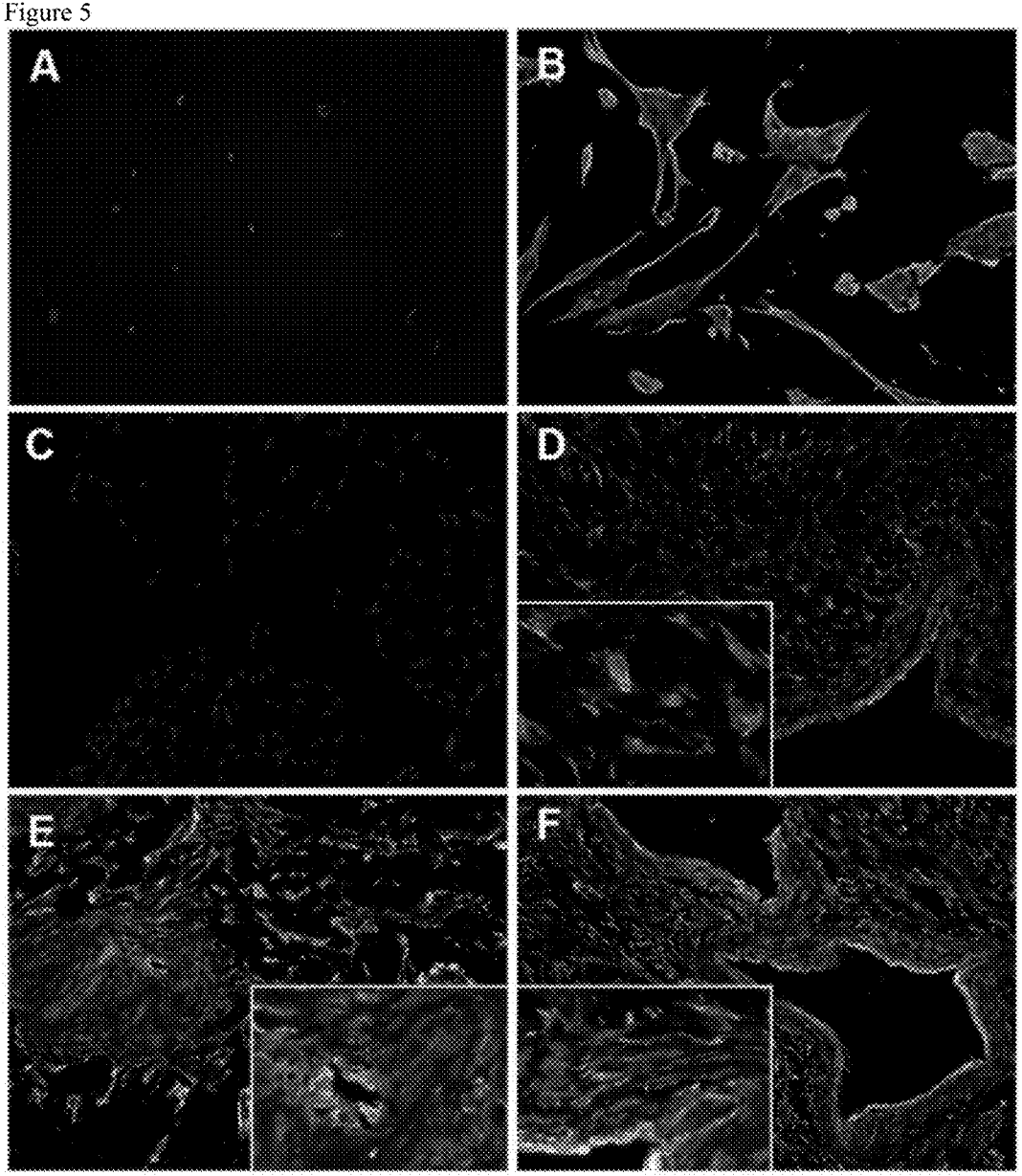
FIG. 5A shows expression of vimentin by hMSC cultured on culture plates.
FIG. 5B shows expression of cytokeratin by hMSC cultured on culture plates.
FIG. 5C shows expression of vimentin by control cells seeded onto a glucomannan scaffold.
FIG. 5D shows expression of vimentin by hMSC cells seeded onto a glucomannan scaffold.
FIG. 5E shows expression of vimentin by flat cells lining irregularly shaped lumens.
FIG. 5F shows expression of vimentin by flat cells lining irregularly shaped lumens.
Figure 6:
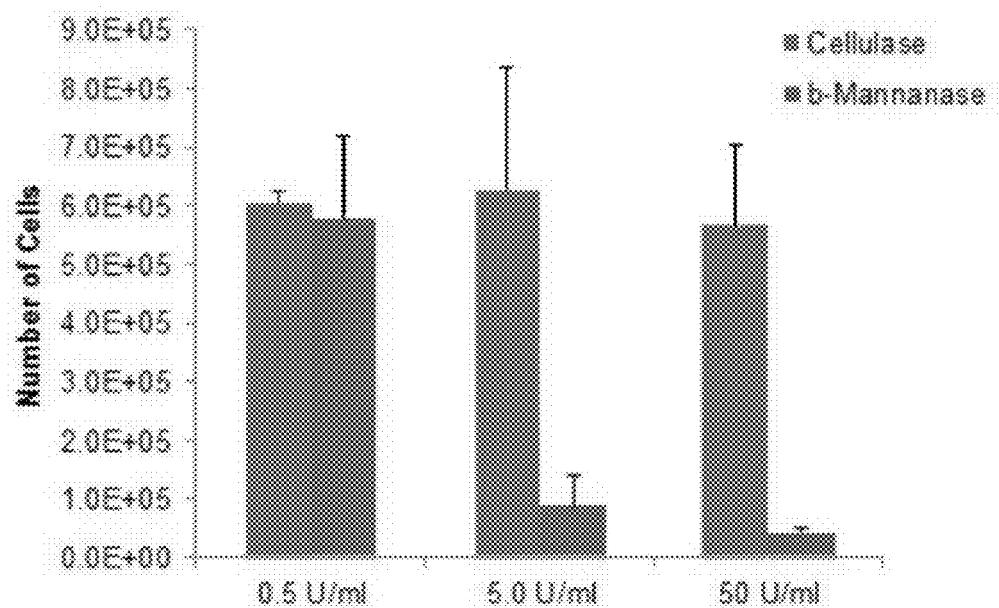
FIG. 6A shows cellular aggregates released from enzymatic digestion of a seeded glucomannan scaffold.
FIG. 6B shows an outgrowth of cells observed on the cellular aggregates of FIG. 6A after washing and culturing overnight.
FIG. 6C shows cellular release from enzymatic digestion of a seeded glucomannan scaffold. Glucomannan scaffolds seeded with rhMSC were digested with 0.5, 5.0 and 50 units/ml of cellulase or β-mannanase, and cells released from the scaffold were trypsinzed and counted. Scaffolds incubated with cellulase showed an efficient release of cells at all concentrations. However, higher concentrations of β-mannanase resulted in suboptimal cell counts, whereas 0.5 unit/ml showed results similar to cellulose.
Figure 6:
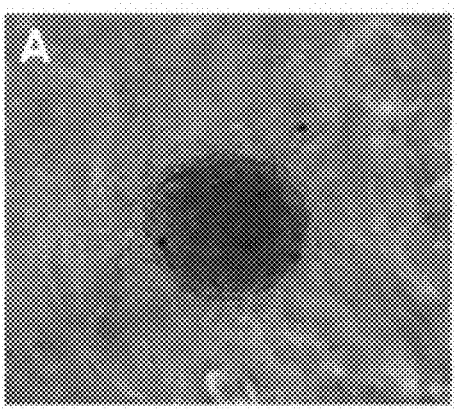
Figure 6:
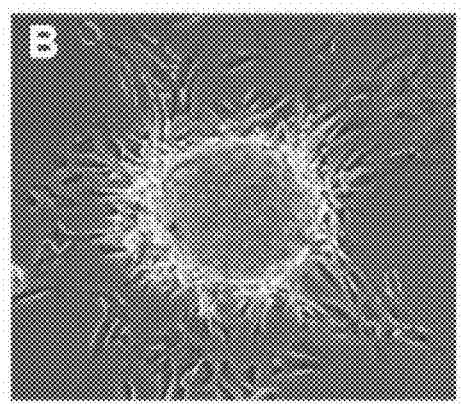
Figure 7:
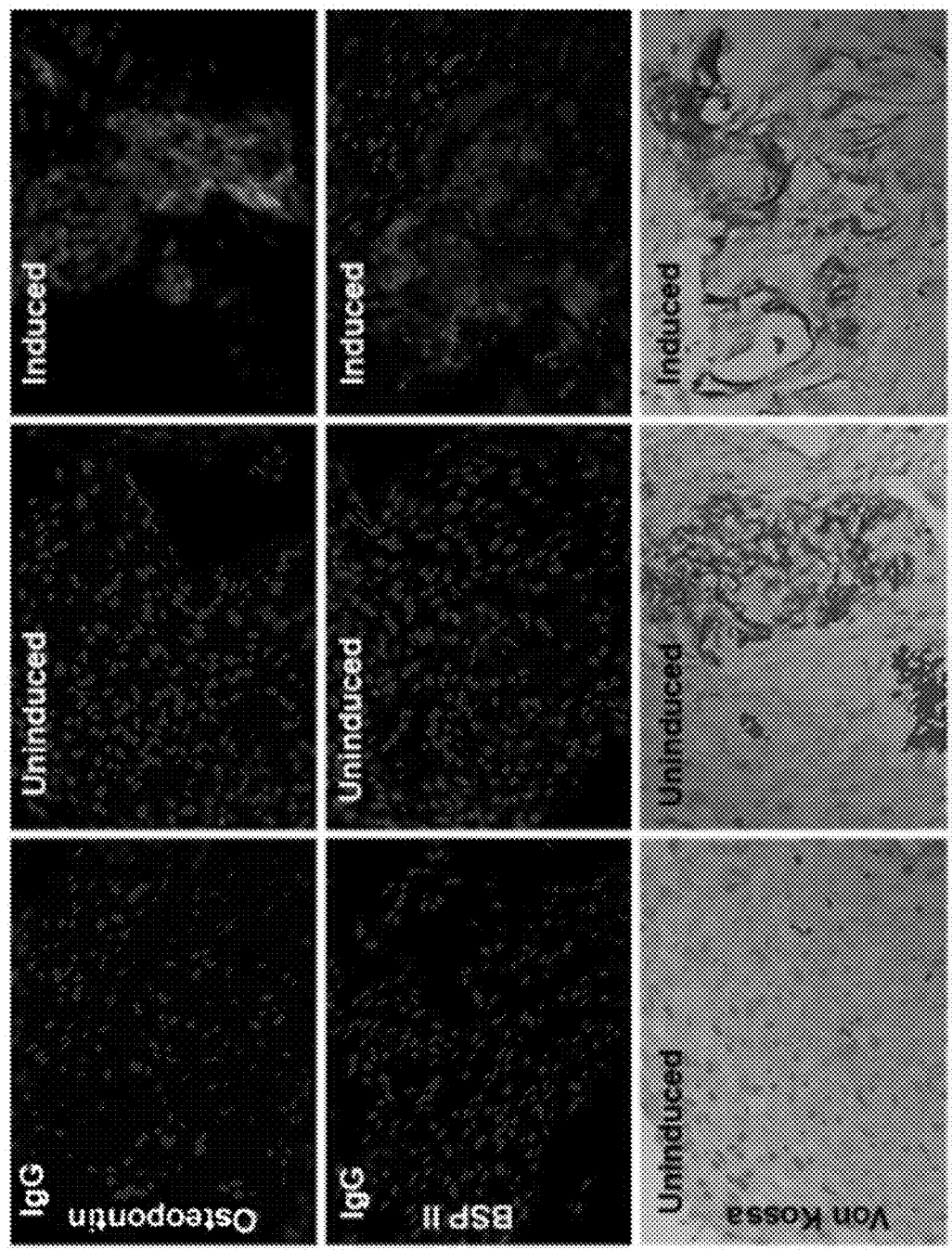
FIG. 7 shows osteogenic differentiation of hMSC seeded onto glucomannan scaffolds. rhMSC seeded onto glucomannan scaffolds and cultured with and without osteogenic induction medium were stained with antibodies against human osteopontin and bone sialoprotein II (BSP II). Induced hMSC showed both osteopontin and BSP II expression. Uninduced cells initiated BSP II expression. Von Kossa staining showed mineral deposits in both uninduced and induced scaffolds. Magnification=10×.
Figure 8A:
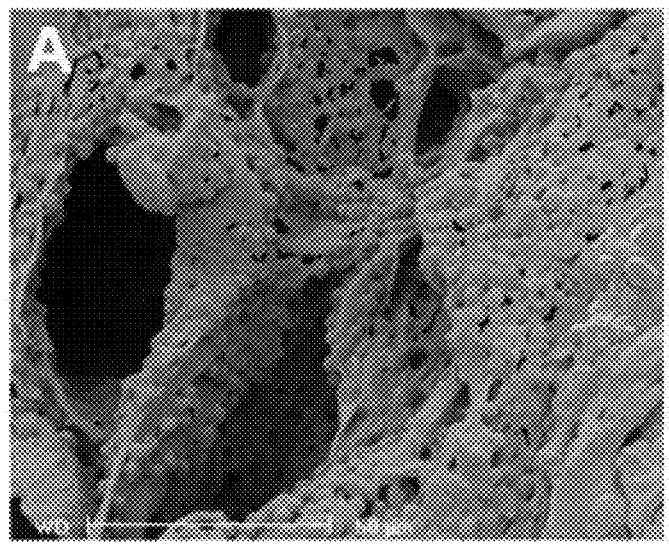
FIG. 8A shows a scanning electron micrograph of CD34+ cell adherence to hMSC seeded onto glucomannan scaffolds and co-cultured with CD34+ hematopoietic cells.
Figure 8B:
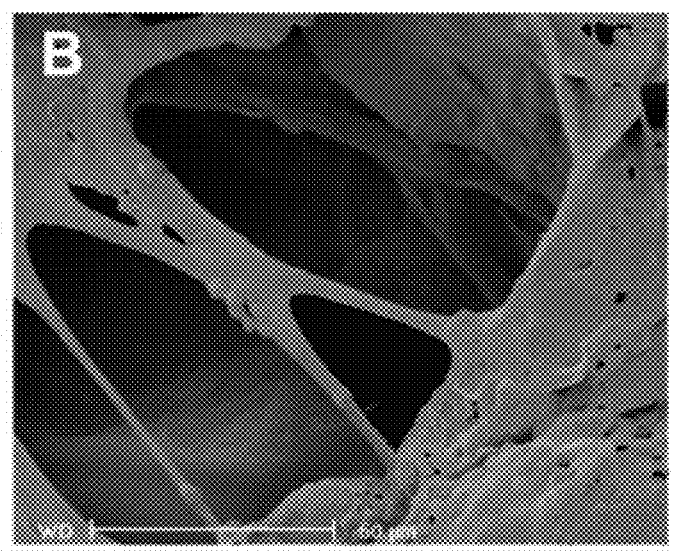
FIG. 8B shows a scanning electron micrograph of the ability of hMSC to "bridge" a pore in a glucomannan scaffold co-cultured with hMSC and CD34+ hematopoietic cells.
Figure 8C:
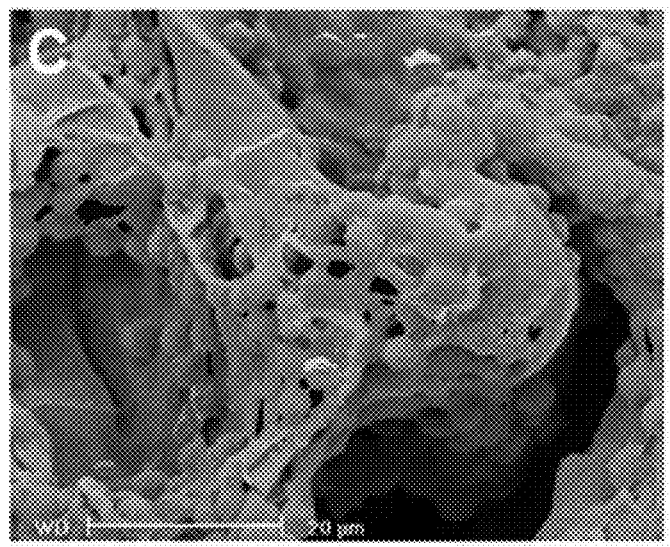
FIG. 8C shows a scanning electron micrograph of CD34+ cell adherence to hMSC seeded onto glucomannan scaffolds and co-cultured with CD34+ hematopoietic cells.
Figure 8D:
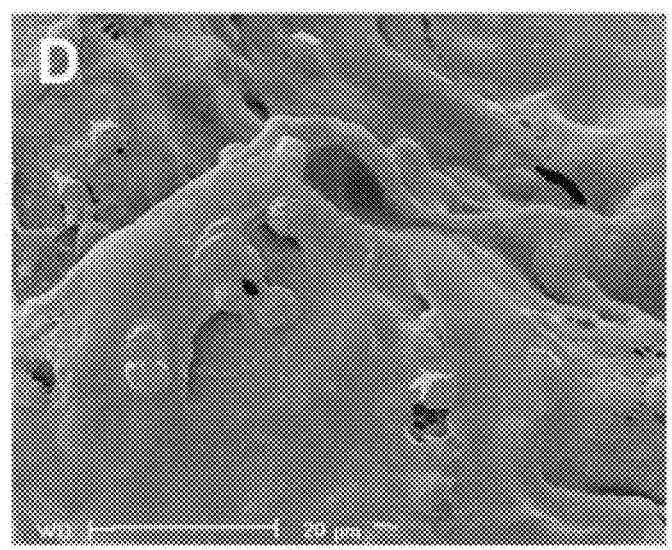
FIG. 8D shows a scanning electron micrograph of CD34+ cell adherence to hMSC seeded onto glucomannan scaffolds and co-cultured with CD34+ hematopoietic cells.
Figure 9:
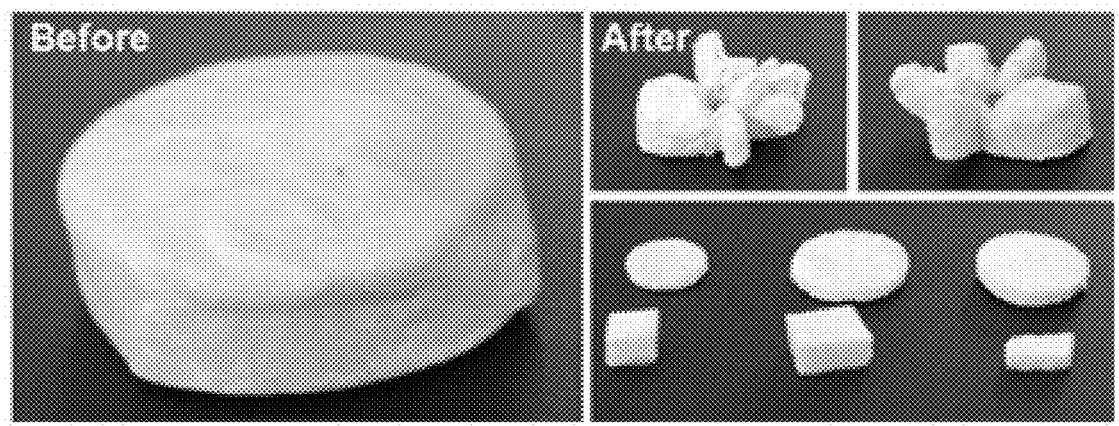
FIG. 9 shows a glucomannan scaffold before and after fabrication. This image can be a part of Example 1. A glucomannan scaffold was fabricated into a shape of a vertebra (top right) and various shapes to fit into cell and culture vessels using either a knife or biopsy punch. This figure provides a proof-of-concept example showing the scaffold of this invention can be fabricated into a variety of shapes resembling different organ systems.
Figure 10:
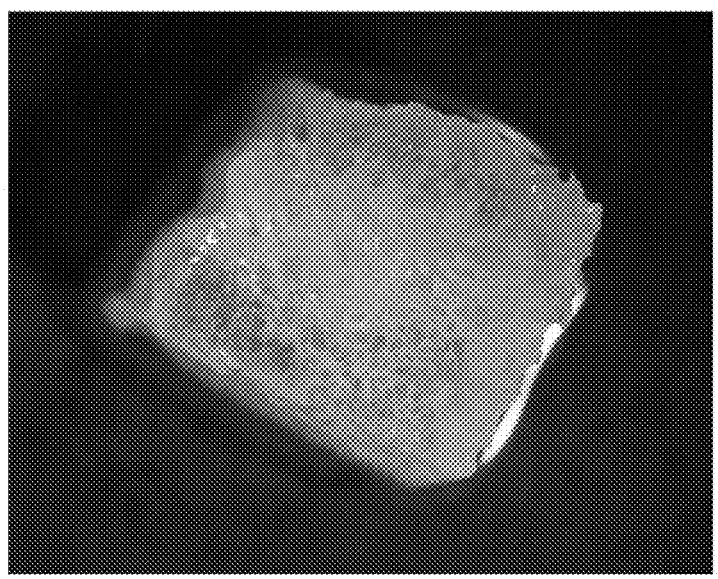
FIG. 10 shows a gross image of a three-dimensional bone construct produced using the neutralized glucomannan scaffold and human stem cells.

As used herein, the term "glucomannan" refers to a naturally-derived oligosaccharide composed of an approximately 1:1.6 ratio of β-1,4-linked D-glucose to D-mannose with branches approximately every 11 residues (Alonso-Sande et al. *Eur J Pharm Biopharm.* 2009 72:453-462) and derivatives thereof. Glucomannan has a backbone of approximately 5-10% substituted acetyl groups that participate in hydrogen bonding and hydrophobic interactions that confer solubility. Exemplary glucomannan derivatives include, but are not limited to, water-soluble derivatives such as O-alkyl derivatives and O-carboxyalkyl derivatives, derivatives with various degrees of substitution (e.g., greater than or less than 5-10% substituted acetyl groups), derivatives with various degrees of oxidation, graft copolymers (e.g., acrylate and acrylamide copolymers) and salts thereof (e.g., quaternary ammonium salts thereof).

As used herein, the term "glucomannan gel" refers to a thermally stable, homogeneous suspension of crosslinked glucomannan. The glucomannan gel can be formed in a variety of ways including, but not limited to, by hydrolysis of the acetyl groups of glucomannan in the presence of alkali. The glucomannan gel of the present invention can be modified to promote cell adhesion and proliferation. Exemplary modifications include, but are not limited to, incorporation of a cell adhesion promoter, chemical crosslinking, surface coating and introduction of functional groups.

As used herein, the term "basic glucomannan scaffold" refers to a three-dimensional porous matrix formed by dehydrating a glucomannan gel and having a pH of greater than about 8. The basic glucomannan scaffold of the present invention may be modified to promote cell adhesion and proliferation. Exemplary modifications include, but are not limited to, incorporation of a cell adhesion promoter, surface coating, and introduction of functional groups.

As used herein, the term "neutralized glucomannan scaffold" refers to a porous matrix that provides a three-dimensional environment suitable for cell culture and tissue engineering, including tissue regeneration, and having a pH of about 7. The neutralized glucomannan scaffold of the present invention is formed by neutralizing a basic glucomannan scaffold with an aqueous solution. The neutralized glucomannan scaffold of the present invention may be modified to promote cell adhesion and proliferation.

As used herein, the term "contacting" refers to the process of bringing into contact at least two distinct species such that they can react. It should be appreciated, however, that the resulting reaction product can be produced directly from a reaction between the added reagents or from an intermediate from one or more of the added reagents which can be produced in the reaction mixture.

As used herein, the term "cell adhesion promoter" refers to a natural or synthetic agent that enhances the adhesion or attachment of cells to a culture substrate, for example, by modifying the surface of the substrate, and/or by altering the surface charge. A cell adhesion promoter may also enhance the adsorption of serum or extracellular matrix proteins to the culture substrate. Exemplary cell adhesion promoters include poly-L-lysine (PLL), poly-D-lysine (PDL), RGD peptide (RGD), KQAGDV, VAPG, FGL, amine groups, and extracellular matrix proteins such as fibronectin, elastin, collagen and laminin. The cell adhesion promoter can also promote cell growth and cell differentiation.

As used herein, the term "buffered solution" refers to a homogeneous mixture of a buffer, or ionic compound that is a mixture of a weak acid and its conjugate base or a weak base and its conjugate acid and resists changes in pH, in water. Exemplary buffers include, but are not limited to, phosphate buffers, such as phosphate buffered saline (PBS), 3-{[tris(hydroxymethyl)methyl]amino}propanesulfonic acid (TAPS) 1,3-bis(tris(hydroxymethyl)methylamino)propane (BIS-TRIS), tris(hydroxymethyl)methylamine (TRIS), 4-2-hydroxyethyl-1-piperazineethanesulfonic acid (HEPES), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES) and 2-(N-morpholino)ethanesulfonic acid (MES).

As used herein, the term "acidic solution" refers to a homogeneous mixture of an acid, or substance that acts as a proton donor, in water. An acidic solution has a pH of less than 7. Exemplary acidic solutions include, but are not limited to, hydrochloric acid, acetic acid, tartaric acid, malic acid and citric acid.

As used herein, the term "alkaline solution" refers to a basic solution containing the salt of an alkali metal or alkaline earth metal, having a pH greater than 7. Representative salts of alkali and alkali earth metals include, but are not limited to, sodium hydroxide, sodium carbonate, potassium hydroxide, potassium carbonate, magnesium hydroxide, magnesium carbonate, calcium hydroxide and calcium carbonate.

As used herein, the term "cell culture medium" refers to a substance that supports the growth of cells. A cell culture medium typically contains a mixture of nutrients dissolved in a buffered solution, and different types of cell culture media are useful for growing different types of cells. Exemplary cell culture media include, but are not limited to, Roswell Park Memorial Institute medium (RPMI), Dulbecco's Modified Eagle Medium (DMEM), Minimum Essential Medium (MEM), Dulbecco's Modified Eagle Medium: Nutrient Mixture F-12 medium (DMEM/F12), Iscove's Modified Dulbecco's Medium (IMDM), a National Collection of Type Cultures medium (NCTC) and Osteogenic Induction Medium (OIM).

As used herein, the term "degrading" refers to the breaking of the crosslinking bonds that hold the scaffold together. The degrading is accomplished using a degrading agent that hydrolyzes the glycosidic linkages. The scaffold degrading agent can be any chemical or enzyme, such as endo-1,4 β-mannanase, mannan endo-1,4-β-mannosidase, glycosyl hydrolase or cellulase, that does not digest cells attached to or embedded in a neutralized glucomannan scaffold. Other enzymes are useful in the present invention.

II. Neutralized Glucomannan Scaffold

The present invention provides a neutralized glucomannan scaffold as a novel scaffold for three-dimensional cell culture and tissue engineering. The neutralized glucomannan scaffold provides a neutral environment and a highly porous structure and pore size suitable for culturing cells. The neutralized glucomannan scaffold can incorporate a cell adhesion promoter. Moreover, the scaffold is homogenous, thermally stable, elastic, biocompatible and biodegradable, and can be made into any shape and size suitable for 3D tissue culture and engineering by, for example, molding or cutting. The neutralized glucomannan scaffold can also be sterilized by autoclaving, making it useful for implantation and other in vivo applications.

Unlike alginate-based scaffolds (e.g., AlgiMatrix), the size of the neutralized glucomannan scaffold is not limited. In addition, the neutralized glucomannan scaffold can be modified for cell adherence in a single step compared to the requirement for multiple, complex chemical reactions for modifying alginate-based scaffolds.

The neutralized glucomannan scaffold can be prepared by any conditions suitable to neutralize a basic glucomannan scaffold. Suitable conditions, for example, are those that can reduce the pH of the glucomannan scaffold from about 8 or greater, to about 7, in a suitable amount of time. For example, the basic glucomannan scaffold can be exposed to an aqueous solution in a heated environment, such as in an autoclave. Alternatively, suitable conditions involves continuous rinsing of the basic glucomannan scaffold using an aqueous solution for a suitable amount of time.

In some embodiments, the present invention provides a method for preparing a neutralized glucomannan scaffold, including contacting a basic glucomannan scaffold having a pH of greater than about 8 with an aqueous solution at a pressure greater than or about atmospheric pressure, to form the neutralized glucomannan scaffold having a pH of about 7, thereby preparing the neutralized glucomannan scaffold.

The basic glucomannan scaffold can have any suitable pH equal to or greater than about 8.0. Examples of suitable pH include about 8.0, 8.5, 9.0, 9.5, 10.0, 10.5, 11.0 and higher.

The neutralized glucomannan scaffold can have any suitable pH of about 7. Examples of suitable pH include from about 6.0 to about 8.0, such as from about 6.1 to about 7.9, from about 6.2 to about 7.8, from about 6.3 to about 7.7, from about 6.4 to about 7.6, and from about 6.5 to about 7.5.

The contacting can be performed at any suitable temperature. For example, the temperature can be room temperature, greater than room temperature or less than room temperature. In some embodiments, the temperature is suitable to form steam. In some embodiments, the temperature can be from about 0° C. to about 200° C., or from about 20° C. to about 200° C., or from about 20° C. to about 150° C., or from about 0° C. to about 130° C., or from about 20° C. to about 130° C., or from about 20° C. to about 100° C., or from about 20° C. to about 50° C., or from about 30° C. to about 50° C., or from about 50° C. to about 200° C., or from about 75° C. to about 150° C., or from about 100° C. to about 150° C. The temperature can also be about 0° C., 5, 10, 15, 20, 25, 30, 35, 40, 45, 50, 60, 70, 80, 90, 100, 110, 120, 130, 140, 150, 160, 170, 180, 190 or about 200° C. The temperature can also be about 30, 31, 32, 33, 34, 35, 36, 37, 38, 39, 40, 41, 42, 43, 44 or 45° C. In some embodiments, the contacting can be performed at a temperature of from about 0° C. to about 130° C. In other embodiments, the contacting can be performed at a temperature of from about 20° C. to about 50° C. In still other embodiments, the contacting can be performed at a temperature of about 37° C. In some embodiments, the temperature is about room temperature.

The contacting can be performed at any suitable pressure. In some embodiments, the contacting can be performed under reduced or increased pressure. In some embodiments, the contacting is performed above atmospheric pressure. In some embodiments, the contacting can be performed at a pressure of from about 0.1 psi to about 50 psi above atmospheric pressure. In some embodiments, the contacting can be performed at a pressure of from about 1 psi to about 50 psi above atmospheric pressure. Other useful pressures include about 5, 10, 15, 20, 25, 30, 35, 40, or about 45 psi above atmospheric pressure. In another embodiment, the contacting is performed at a pressure of from about 1 psi to about 30 psi above atmospheric pressure. In still other embodiments, the contacting is performed at a pressure of from about 10 psi to about 20 psi above atmospheric pressure. In some embodiments, the contacting is performed at a pressure of about 15 psi above atmospheric pressure.

Any combination of temperature and pressure can be used to neutralize the basic glucomannan scaffold. For example, the temperature can be sufficient to generate steam, such as greater than 100° C., and the pressure can be greater than atmospheric pressure, such as from about 0.1 psi to about 50 psi above atmospheric pressure. Other combinations of temperature and pressure are useful in the present invention, such as at atmospheric temperature and pressure.

The contacting can be performed for any suitable period of time. In some embodiments, the period of time can be from about 1 minute to about 1 month. In other embodiments, the contacting can be performed for from about 1 hour to about 1 week. In other embodiments, the contacting can be performed for from about 1 hour to about 1 day. In still other embodiments, the contacting can be performed for from about 8 to about 20 hours.

The basic glucomannan scaffold can include a variety of other components. For example, cell adhesion promoters, chemotactic molecules and cell signaling molecules can be incorporated in the basic glucomannan scaffold.

In some embodiments, the basic glucomannan scaffold includes a suitable cell adhesion promoter. The cell adhesion promoters useful in the present invention are capable of adhering cells to the glucomannan scaffold. The cell adhesion promoters can also promote cell growth and/or promote cell differentiation. Exemplary cell adhesion promoters include, but are not limited to, poly-L-lysine (PLL), poly-D-lysine (PDL), RGD peptide (RGD), KQAGDV, VAPG, FGL, amine groups, and extracellular matrix proteins such as fibronectin, elastin, collagen and laminin. In some embodiments, the cell adhesion promoter can be poly-L-lysine (PLL), poly-D-lysine (PDL), RGD peptide (RGD), KQAGDV, VAPG, FGL, amine groups, fibronectin, elastin, collagen or laminin. The extracellular matrix proteins can be from any suitable source, including, but not limited to, mammalian cells. In some embodiments, the cell adhesion promoter is PLL or RGD. In certain embodiments, the cell adhesion promoter is PLL.

In some embodiments, the present invention provides a method for preparing a neutralized glucomannan scaffold, including contacting a basic glucomannan scaffold having a pH of greater than about 8 with an aqueous solution to form the neutralized glucomannan scaffold having a pH of about 7, wherein the basic glucomannan scaffold comprises a cell adhesion promoter, thereby preparing the neutralized glucomannan scaffold.

In another embodiment, the basic glucomannan scaffold includes a suitable chemotactic molecule. Exemplary chemotactic molecules include, but are not limited to, serum, chemokines, morphogenetic proteins, growth factors, hyaluronan.

In another embodiment, the basic glucomannan scaffold includes a suitable cell signaling molecule. Exemplary cell signaling molecules include, but are not limited to, extraceullar matrix proteins, peptide motifs and growth factors.

The aqueous solution can have any suitable composition. The aqueous solution can be water or a mixture of water and one or more non-alkaline agents that do not degrade or digest the neutralized glucomannan scaffold. Examples of suitable aqueous solution include, but are not limited to, water, a buffered solution, an acidic solution and a cell culture medium. In some embodiments, the aqueous solution is water, a buffered solution, an acidic solution or a cell culture medium.

In one embodiment, the aqueous solution is a buffered solution. Examples of suitable buffered solutions include, but are not limited to, PBS, TAPS, BIS-TRIS propane, TRIS, HEPES, TES, MOPS, PIPES and MES. In some embodiments, the buffered solution is PBS, HEPES, MES, MOPS, TRIS or BIS-TRIS Propane. In certain embodiments, the buffered solution is PBS.

In another embodiment, the aqueous solution is an acidic solution. Examples of suitable acidic solutions include, but are not limited to, such as, but not limited to, hydrochloric acid, acetic acid, tartaric acid, malic acid and citric acid.

In another embodiment, the aqueous solution is a cell culture medium. Examples of suitable cell culture media include, but are not limited to, Roswell Park Memorial Institute medium (RPMI), Dulbecco's Modified Eagle Medium (DMEM), Minimum Essential Medium (MEM), Dulbecco's Modified Eagle Medium: Nutrient Mixture F-12 medium (DMEM/F12), Iscove's Modified Dulbecco's Medium (IMDM), a National Collection of Type Cultures medium (NCTC) and Osteogenic Induction Medium (OIM). In some embodiments, the cell culture medium is Roswell Park Memorial Institute medium (RPMI), Dulbecco's Modified Eagle Medium (DMEM), Minimum Essential Medium (MEM), Dulbecco's Modified Eagle Medium: Nutrient Mixture F-12 medium (DMEM/F12), Iscove's Modified Dulbecco's Medium (IMDM) or a National Collection of Type Cultures medium (NCTC).

The method of the invention can include a variety of additional steps. In some embodiments, the method further includes forming a reaction mixture including glucomannan powder, an alkaline solution and water; heating the reaction mixture at a temperature of from about 50° C. to about 130° C. to form a glucomannan gel; increasing the pressure of the glucomannan gel to from about 0.1 psi to about 50 psi above atmospheric pressure; cooling the glucomannan gel to a temperature of less than about 50° C.; and removing the water from the glucomannan gel to form the basic glucomannan scaffold. The basic glucomannan scaffold can be further modified with a cell adhesion promoter described above.

The method of the invention can include a variety of additional steps. In some embodiments, the method further includes forming a reaction mixture including glucomannan powder, a cell adhesion promoter, an alkaline solution and water; heating the reaction mixture at a temperature of from about 50° C. to about 130° C. to form a glucomannan gel; increasing the pressure of the glucomannan gel to from about 0.1 psi to about 50 psi above atmospheric pressure; cooling the glucomannan gel to a temperature of less than about 50° C.; and removing the water from the glucomannan gel to form the basic glucomannan scaffold.

The alkaline solution can be any solution containing the salt of an alkali metal or alkaline earth metal. The alkaline solution is basic, having a pH greater than 7. Representative salts of alkali and alkali earth metals include, but are not limited to, sodium hydroxide, sodium carbonate, potassium hydroxide, potassium carbonate, magnesium hydroxide, magnesium carbonate, calcium hydroxide and calcium carbonate. In some embodiments, the alkaline solution comprises calcium hydroxide.

Glucomannan powder, the cell adhesion promoter and calcium hydroxide can each be present in the reaction mixture in any suitable amount. In some embodiments, glucomannan powder is dissolved in water to provide a glucomannan solution containing from about 1% to about 5% w/v glucomannan in water.

In other embodiments, a cell adhesion promoter is added to the glucomannan solution as an aqueous solution containing from about 0.0001% to about 20% w/v cell adhesion promoter. In one embodiment, a cell adhesion promoter is added to the glucomannan solution as an aqueous solution containing from about 0.0001% to about 10% w/v cell adhesion promoter. In another embodiment, a cell adhesion promoter is added to the glucomannan solution as an aqueous solution containing from about 0.0001% to about 1% w/v cell adhesion promoter.

In still other embodiments, calcium hydroxide is added to the glucomannan solution in an amount to provide any suitable ratio of calcium hydroxide to glucomannan solution. For example, the ratio of calcium hydroxide to glucomannan solution can be from about 1:1000 to about 1:1 (w/w). In one embodiment, the ratio is 1:10 (w/w). In another embodiment, calcium hydroxide is added to the glucomannan solution as an aqueous solution containing from about 1% to about 2% w/v calcium hydroxide.

The reaction mixture can be formed at any suitable temperature, such as those described above for the contacting step.

The reaction mixture can be heated to any suitable temperature. In some embodiments, the temperature can be greater than about 20, 25, 30, 35, 40, 45, 50, 55, 60, 65, 70, 75, 80, 85, 90, 95, 100, 105, 110, 115, 120, 125, 130° C. or higher. In some embodiments, the reaction mixture can be heated at a temperature of greater than about 130° C. In some embodiments, the reaction mixture can be heated to a temperature of greater than about 80° C.

The pressure of the glucomannan gel can be increased to any suitable pressure. In some embodiments, the pressure can be increased to from about 0.1 psi to about 200 psi above atmospheric pressure. In other embodiments, the pressure is increased to from about 0.1 psi to about 50 psi above atmospheric pressure. In certain embodiments, the pressure is increased to about 30 psi.

The temperature of the glucomannan gel can be cooled to any suitable temperature. In some embodiments, the temperature is cooled to about less than 80° C. In certain embodiments, the temperature is cooled to less than about 50° C.

The water can be removed from the glucomannan gel by any suitable method. In some embodiments, the removing step is performed by freeze-drying, sublimation or thermally-induced phase separation work. In certain embodiments, the removing step is performed by sublimation.

The neutralized glucomannan scaffold can have any suitable pore size. In some embodiments, the neutralized glucomannan scaffold has a pore size of from about 100 μm to about 400 μm. In other embodiments, the neutralized glucomannan scaffold can have a pore size of about 150 μm to about 350 μm. In still other embodiments, the neutralized glucomannan scaffold can have a pore size of about 200 μm to about 300 μm.

In other embodiments, the present invention provides a method of preparing a neutralized glucomannan scaffold, including contacting a basic glucomannan scaffold having a pH of greater than about 8 with an aqueous solution at a pressure greater than or about atmospheric pressure, to form the neutralized glucomannan scaffold having a pH of about 7, thereby preparing the neutralized glucomannan scaffold.

The contacting can also be performed under any suitable vacuum pressure. In some embodiments, the contacting can be performed under a vacuum pressure of from about 0.1 mmHg to 760 mmHg. In some embodiments, the contacting can be performed at a vacuum pressure of from about 10 mmHg to about 500 mmHg. Other useful vacuum pressures include about 20, 50, 100, 200, 300, 400, or 500 mmHg. In another embodiment, the contacting is performed under a vacuum pressure of from about 10 psi to about 300 mmHg. In still other embodiments, the contacting is performed at a vacuum pressure of about 400 mmHg.

In another embodiment, the present invention provides a neutralized glucomannan scaffold, prepared by contacting a basic glucomannan scaffold having a pH of greater than about 8, with an aqueous solution to form the neutralized glucomannan scaffold having a pH of about 7.

In another embodiment, the present invention provides a neutralized glucomannan scaffold, prepared by contacting a basic glucomannan scaffold having a pH of greater than about 8, with an aqueous solution to form the neutralized glucomannan scaffold having a pH of about 7, wherein the basic glucomannan scaffold comprises a cell adhesion promoter.

The present invention also provides a method of degrading the neutralized glucomannan scaffold of the present invention, by contacting the neutralized glucomannan scaffold with a degrading agent. The degrading agent can be any suitable agent capable of hydrolyzing the glycosidic linkages. The degrading agent can be any chemical or enzyme. Enzymes useful as a degrading agent include, but are not limited to, endo-1,4 β-mannanase, mannan endo-1,4-β-mannosidase, glycosyl hydrolase and cellulase. Other degrading agents include, but are not limited to, enzymes such as mannanase, pectinase, xylanase, glucanase, galactanase, or others.

The present invention also provides a composite scaffold comprising the neutralized glucomannan scaffold of the invention and a suitable biomaterial. Suitable biomaterials include, protein- and polysaccharide-based biomaterials and polymer-, peptide- and ceramic-based biomaterials. Exemplary biomaterials include, but are not limited to, extracellular matrix proteins (e.g., fibronectin elastin, collagen and laminin), alginate, chitosan, hyaluronic acid, Matrigel, gelatin, hydroxyapatite, calcium phosphates and bioactive glasses.

The methods of the present invention can be used to prepare a variety of glucomannan scaffolds. In some embodiments, the present invention provides a neutral glucomannan scaffold. The neutral glucomannan scaffold can have a pH of about 7.

In some embodiments, the glucomannan scaffold can be a basic glucomannan scaffold having a pH equal to or greater than about 8.

In some embodiments, the glucomannan scaffold includes a cell adhesion promoter. Any suitable cell adhesion promoter can be used in the present invention, such as those described above. In some embodiments, the cell adhesion promoter can be poly-L-lysine (PLL), poly-D-lysine (PDL), RGD peptide (RGD), KQAGDV, VAPG, FGL, amine groups, fibronectin, elastin, collagen or laminin. In some embodiments, the cell adhesion promoter can be poly-L-lysine (PLL).

As described above, the glucomannan scaffold of the present invention can be prepared by a variety of methods, such as those described above. In some embodiments, the glucomannan scaffold of the present invention is prepared by the methods of the present invention.

III. Growing Cells

The neutralized glucomannan scaffold of the present invention is useful for growing cells. Cells cultured on the neutralized glucomannan scaffold can interact with other cells and cell types and form aggregates. Cell adherence to and proliferation on the neutralized glucomannan scaffold can be promoted by incorporation of a cell adhesion promoter. Long-term culture is supported by the neutralized glucomannan scaffold. When cultured on the neutralized glucomannan scaffold, cells can undergo proliferation and differentiation. For example, stem cells can differentiate into functional lineages such as bone cells, cartilage, skin cells and blood cells. Accordingly, cellular processes such as osteogenesis, chondrogenesis and hematopoiesis can be supported on the neutralized glucomannan scaffold.

In another embodiment, the present invention provides a method of growing cells on a neutralized glucomannan scaffold, including heating a reaction mixture of the neutralized glucomannan scaffold of the present invention and a cell, such that the cell multiplies, thereby growing cells on the neutralized glucomannan scaffold. The cells can be grown in vivo or in vitro.

Suitable cell types include, but are not limited to, somatic cells, such as fibroblasts, skin cells, endothelial cells, epithelial cells, osteocytes, hepatocytes, neurons and chondrocytes, and stem and progenitor cells, such as endothelial progenitor cells, embryonic stem cells, induced pluripotent stem cells, mesenchymal stem cells, hematopoietic stem cells, neuronal stem cells and muscle stem cells, and their derivatives. In some embodiments, the cell is a somatic cell. In other embodiments, the cell is a stem cell or a progenitor cell. In certain embodiments, the cell is a stem cell. In certain other embodiments, the cell is a derivative of a stem cell.

The cells grown on the neutralized glucomannan scaffold can be recovered by dissolving the glucomannan scaffold using any suitable agent. For example, the glucomannan scaffold can be dissolved using on or more enzymes such as mannanase, cellulase, pectinase, xylanase, glucanase, galactanase, or others. Other agents for dissolving the glucomannan scaffold are known to those of skill in the art.

IV. Examples

Example 1: Preparation of Glucomannan Scaffold

Glucomannan powder (1-5 g) was dissolved in 100 ml of distilled water and stirred slowly for 5 min, then the solution was incubated at room temperature for 60 min. Calcium hydroxide solution (1.5%, 10 ml; Sigma-Aldrich, St. Louis, Mo., USA) was added to the glucomannan solutions and mixed vigorously for 1 min. Poly-L-lysine (Sigma-Aldrich) (0.001% to 1% w/v aqueous solution) was added to the mixture and heated to 125° C. in a decloaking chamber for 30 min. After cooling to room temperature, glucomannan gels were soaked in distilled water overnight. Glucomannan gels were placed in culture dishes and then frozen in a blast freezer for 30 min at less than or equal to −50° C. Water was sublimated using a Vitris model 50-SRC-5 Sublimator. The shelf temperature was 12° C. with a condenser temperature of less than or equal to −58° C., and the vacuum was maintained at 80-100 millitorr. The resulting glucomannan products were then packed in polyethylene bags, vacuum-sealed, and stored at less than or equal to −20° C. until use.

Neutralizing Glucomannan Scaffold

Water Rinse Prior to Sublimation.

Prior to sublimation of water, the glucomannan gel was washed several times in a large volume of water (approximately 5 liters) overnight (16-24 hours). After sublimation of water, the glucomannan scaffold was soaked in water, and the scaffold was pressed against a pH indicator. The scaffold showed a pH greater than 10. This indicated that washing of the glucomannan gel prior to sublimation of water and brief soaking of the glucomannan scaffold in water after sublimation of water were insufficient for neutralizing the scaffold.

Conventional PBS Wash.

The glucomannan scaffold was washed in PBS once or three times. This resulted in superficial (surface only) neutralization of the scaffold with an internal pH of greater than 9 or 10. The glucomannan scaffold was also washed in PBS for 10, 30, and 60 minutes. In all cases, these approaches resulted in superficial neutralization of the scaffold as described above. These findings indicated that conventional washing of the scaffold in a buffered solution was insufficient for neutralization of the scaffold essential for culturing mammalian cells.

Heated PBS Wash.

The glucomannan scaffold was then incubated in PBS at 95-100° C. for 30 minutes. A visible shrinkage of the scaffold was noted. After 30 minutes in boiling PBS, the scaffold was cut and pressed against a pH indicator. The outer region of the scaffold showed a neutral pH. However, the center of the scaffold showed condensation of the scaffold material, and this central region remained outside of the neutral range. In all cases described above, the scaffold stayed afloat indicating the presence of internal air pockets. Even after treating with boiling PBS for 30 minutes, the scaffold stayed afloat with a notable undesired change in the shape. These findings indicated that PBS had not completely displaced air trapped inside the scaffold, which led to insufficient neutralization.

Pressurized PBS Wash.

The glucomannan scaffold was transferred to a beaker containing PBS and incubated at 120° C. in a pressurized chamber at 15 psi above atmospheric pressure for 30 minutes. No shrinkage of the scaffold was observed. The scaffold was submerged in PBS indicating a complete displacement of air pockets with PBS. The glucomannan products were cooled and stored in sterile PBS at 4° C. until use. A pH indicator was used to confirm that the pH of the scaffold was neutral. The entire scaffold showed a neutral pH without any change in the shape.

PBS Wash Under Vacuum.

The glucomannan scaffold was placed on a filter, and a vacuum pressure was applied to the bottom of the scaffold at 400 mmHg. 1 ml of PBS was applied to the top of the scaffold 10 times. After the procedure, a pH indicator was used to confirm that the pH of the scaffold was neutral. The entire scaffold showed a neutral pH without any change in the shape.

Example 2: Cell Growth on Neutralized Glucomannan Scaffold

Preparation of Cells. For human mesenchymal stem cells (hMSC), bone marrow mononuclear cells (N=3, 1 female and 2 males, 20-40 yrs of age; Cambrex, East Rutherford, N.J., USA) were plated in 100 mm plates in α-MEM containing 20% fetal bovine serum (FBS), 1% L-glutamine, and 1% penicillin-streptomycin (Invitrogen, Carlsbad, Calif., USA) and incubated at 37° C. in 5% $CO_2$. Plates were washed with phosphate-buffered saline (PBS) three times every other day until cells reached approximately 80% confluence. Cells were incubated with 0.25% trypsin-EDTA (Invitrogen) for 5 min at 37° C. Culture medium was added to the cells in at a 1:1 ratio of trypsin-EDTA in order to inactivate. Cells were replated in culture medium at $5\times10^3$ cells/cm². Cells were cultured up to 3 passages, cryopreserved using a controlled rate protocol at every passage, and stored in liquid nitrogen until use. For CD34+ cells, a subset of bone marrow mononuclear cells mentioned above were incubated with CD34 antibodies conjugated to PE (clone 581, BD Biosciences, San Jose, Calif., USA) in selection buffer (PBS containing 0.5% bovine serum albumin-BSA and 2 mM EDTA in PBS) for 30 min at 4° C. Cells were washed in selection buffer and incubated with anti-PE microbeads (Miltenyi Biotec, Bergisch Gladbach, Germany) for 20 min at 4° C. Cells were washed and resuspended in 500 μL of selection buffer, then applied to separation columns (Miltenyi Biotec). Separation columns were washed three times, and retained cells were eluted with 1 ml of selection buffer. A second round of separation was performed on the eluted cells.

Transduction.

Cryopreserved hMSC from the second passage were thawed and transduced with an HIV-1-derived lentiviral vector ($1\times10^6$ infectious particles/ml) expressing firefly luciferase under the control of the MND promoter in medium containing 4 mg/ml polybrene (Sigma-Aldrich). Cells were incubated overnight, washed with PBS, and replenished with new medium. Cells were cultured until they reached approximately 80% confluence. D-Luciferin was added to a subset of cells at 100 mg/ml, and bioluminescence was measured using a luminometer (Sirius, Berthold, Pforzheim, Germany) to confirm successful transduction.

Cell Seeding and Bioluminescence Imaging.

Glucomannan scaffolds were cut approximately 1 cm×1 cm×0.5 cm (width×depth×height), rehydrated, and washed in PBS 5 times, and incubated in culture medium overnight. hMSC ($1\times10^6$/scaffold) were seeded onto glucomannan scaffolds in a 12-well plate and cultured for 5 weeks. Cells were imaged using an IVIS 200 imaging system (Caliper Life Sciences, Hopkinton, Mass., USA) every 3-4 days for bioluminescence after adding 100 mg/ml of D-luciferin to each well, and images were analyzed using Living Image software (version 3.1, Caliper Life Sciences).

Scanning Electron Microscopy.

Glucomannan scaffolds with and without seeded hMSC were dehydrated in a graded ethanol series. Scaffolds with hMSC were also co-cultured with CD34+ cells ($1\times10^6$) and incubated for 3 days, followed by ethanol dehydration. Samples were mounted onto 12 mm aluminum pin stubs using carbon double sticky tabs, sputter-coated with gold using a PELCO Auto Sputter Coater SC-7, and viewed on the Philips XL30 TMP Scanning Electron Microscope.

Example 3: Enzyme Digestion

Lyophilized endo-1,4 β-mannanase (Megazyme) or cellulase obtained from *Aspergillus niger* (Sigma-Aldrich) were dissolved in culture medium. Scaffolds seeded with hMSC were incubated in 0.5 units/ml, 5.0 units/ml, or 50 units/ml of endo-1,4 β-mannanase or cellulase overnight. Degradation of scaffolds was checked visually. Cells were counted once scaffolds were completely dissolved.

Example 4: Osteogenic Differentiation

Scaffolds seeded with hMSC were incubated in Osteogenic Induction Medium (Cambrex) or culture medium (control) with medium changed every 3-4 days following the manufacturer's recommendations. After 3 weeks, scaffolds were fixed in 10% formalin followed by ethanol dehydration and embedded in paraffin. Scaffolds were sectioned at 6 mm for immunohistochemistry and von Kossa staining.

Immunocytochemistry.

Sections (5-6 μm) were treated with xylene followed by graded concentrations of ethanol. Slides were washed in PBS before heat-mediated antigen retrieval in citrate buffer (pH 6, Invitrogen) was performed. After cooling, decreasing concentrations of warm citrate buffer in PBS was applied followed by incubation with Background Sniper (BioCare Medical, Concord, Calif., USA) which was added to each slide for 15 min. Slides were washed twice with PBS followed by incubation for 1 hr with blocking buffer (1% BSA, 0.1% fish skin gelatin, 0.1% Triton X, 0.05% tween-20) with 2% goat serum (Sigma-Aldrich). After two washes with PBS, primary antibody diluted in primary antibody buffer (1% BSA, 0.1% fish skin gel) was incubated with slides overnight in a humidified chamber at 4° C. Primary antibodies used were wide spectrum rabbit polyclonal anti-human cytokeratin antibody (Abcam, Cambridge, Mass., USA) diluted 1:50 and mouse monoclonal anti-human vimentin antibody (Sigma-Aldrich) diluted 1:100. For bone markers, rat monoclonal anti-human osteopontin antibody and mouse monoclonal anti-human bone sialoprotein II antibody (Millipore, Billerica, Mass., USA) were used at 1:200 dilutions. Mouse, rat, and rabbit IgG isotype controls (Invitrogen) were included. Slides were washed with PBS for 5 min and incubated with secondary antibody for 1 h in the dark at room temperature. Secondary antibodies used were Alexa Fluor 488 goat anti-mouse, Alexa Fluor 954 goat anti-rat, and Alexa Fluor 594 goat anti-rabbit antibodies (Invitrogen) diluted 1:200 in fluorescence antibody diluent (BioCare Medical). After washing twice with PBS, slides were mounted with ProLong Gold® antifade reagent with DAPI (Invitrogen) and a coverslip placed. Slides were observed under an Olympus BX61 microscope.

Von Kossa Staining.

Sections (5-6 µm) were treated with xylene followed by graded concentrations of ethanol. Sections were washed in distilled water and incubated with 1% aqueous silver nitrate solution under ultraviolet light for 1 h, then washed in distilled water and incubated with 5% sodium thiosulfate for 5 min. Sections were washed in distilled water and incubated with 0.1% nuclear fast red solution for 5 min followed by dehydration through graded alcohol and xylene. A coverslip was then placed on the slide in permanent mounting medium and observed under an Olympus BX61 microscope.

Results are reported as the mean±standard error of the mean (SEM) and calculated using Microsoft Excel (Microsoft, Redmond, Wash.). Statistical significance (p<0.05) was determined by two-sided Student's t-test analysis.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of preparing a neutralized glucomannan scaffold, the method comprising contacting a basic glucomannan scaffold having a pH of greater than about 8 with an aqueous solution under vacuum pressure, wherein the aqueous solution is selected from the group consisting of a buffered solution, an acidic solution and a cell culture medium, to form a neutralized glucomannan scaffold having a pH of about 7, thereby preparing the neutralized glucomannan scaffold.

2. The method of claim 1, wherein the contacting is performed at a temperature of from about 0° C. to about 130° C.

3. The method of claim 1, wherein the contacting is performed at a temperature of from about 20° C. to about 50° C.

4. The method of claim 1, wherein the contacting is performed at a temperature of about 37° C.

5. The method of claim 1, wherein the contacting is performed at a pressure of from about 0.1 mmHg to about 760 mmHg.

6. The method of claim 1, wherein the contacting is performed for a period of from about 1 minute to about 1 month.

7. The method of claim 1, wherein the contacting is performed for a period of from about 1 hour to about 1 week.

8. The method of claim 1, wherein the contacting is performed for a period of from about 1 hour to about 1 day.

9. The method of claim 1, wherein the contacting is performed for a period of from about 8 to about 20 hours.

10. The method of claim 1, wherein the basic glucomannan scaffold further comprises a cell adhesion promoter.

11. The method of claim 10, wherein the cell adhesion promoter is selected from the group consisting of poly-L-lysine (PLL), poly-D-lysine (PDL), RGD peptide (RGD), KQAGDV, VAPG, FGL, amine groups, fibronectin, elastin, collagen and laminin.

12. The method of claim 11, wherein the cell adhesion promoter is poly-L-lysine (PLL).

13. The method of claim 10, wherein the method further comprises:
forming a reaction mixture comprising glucomannan powder, the cell adhesion promoter, an alkaline solution and water;
heating the reaction mixture at a temperature of from about 50° C. to about 130° C. to form a glucomannan gel;
increasing the pressure of the glucomannan gel to from about 1 psi to about 200 psi above atmospheric pressure;
cooling the glucomannan gel to a temperature of less than about 50° C.; and
removing the water from the glucomannan gel to form the basic glucomannan scaffold.

14. The method of claim 13, wherein said pressure of the glucomannan gel is increased from about 14.7 psi to about 50 psi above atmospheric pressure.

15. The method of claim 13, wherein said removing step is performed by sublimation.

16. The method of claim 1, wherein the aqueous solution is a buffered solution.

17. The method of claim 16, wherein the buffered solution is selected from the group consisting of PBS, HEPES, MES, MOPS, TRIS and BIS-TRIS Propane.

18. The method of claim 16, wherein the buffered solution is PBS.

19. The method of claim 1, wherein the aqueous solution is a cell culture medium.

20. The method of claim 19, wherein the cell culture medium is selected from the group consisting of a Roswell Park Memorial Institute medium (RPMI), Dulbecco's Modified Eagle Medium (DMEM), Minimum Essential Medium (MEM), Dulbecco's Modified Eagle Medium: Nutrient Mixture F-12 medium (DMEM/F12), Iscove's Modified Dulbecco's Medium (IMDM), a National Collection of Type Cultures medium (NCTC) and Osteogenic Induction Medium (OIM).

* * * * *